United States Patent
Roush et al.

(10) Patent No.: US 6,895,889 B1
(45) Date of Patent: May 24, 2005

(54) AIRBORNE HAZARD DETECTOR

(76) Inventors: Richard J. Roush, 14 Cottonwood Dr., Cabot, AR (US) 72023; Susan L. Roush, 14 Cottonwood Dr., Cabot, AR (US) 72023

( * ) Notice: Subject to any disclaimer, the term of this patent is extended or adjusted under 35 U.S.C. 154(b) by 0 days.

(21) Appl. No.: 10/795,340

(22) Filed: Mar. 9, 2004

(51) Int. Cl.[7] .......................... G09F 11/04; G01D 11/24
(52) U.S. Cl. ...................... 116/307; 116/316; 116/206; 422/58; 422/61; 422/104; 422/169
(58) Field of Search .................... 422/58, 61; 436/104, 436/164, 169; 73/23.2, 31.01, 31.02, 31.03, 31.05; 116/316, 318, 206, 207, 305, 307, 308, 309, 284, 1, 200, 209, DIG. 1

(56) References Cited

U.S. PATENT DOCUMENTS

| 2,994,771 | A | * | 8/1961 | Jones et al. ............... 250/472.1 |
| 3,348,044 | A | * | 10/1967 | Sanders ....................... 250/435 |
| 3,612,870 | A | * | 10/1971 | Brennan .................. 250/473.1 |
| 4,155,326 | A | * | 5/1979 | Ellis ............................ 116/307 |
| 4,303,857 | A | * | 12/1981 | Inoue et al. ................. 250/328 |
| 4,428,907 | A | | 1/1984 | Heijenga et al. .............. 422/61 |
| 4,704,535 | A | * | 11/1987 | Leber et al. ................. 250/372 |
| 4,818,491 | A | * | 4/1989 | Fariss ........................... 422/56 |
| 4,847,199 | A | * | 7/1989 | Snyder et al. ............. 435/7.34 |
| 4,913,881 | A | * | 4/1990 | Evers ........................... 422/56 |
| 5,035,860 | A | | 7/1991 | Kleingeld et al. ............ 422/61 |
| 5,280,834 | A | | 1/1994 | Berkley ....................... 206/5.1 |
| 5,441,698 | A | | 8/1995 | Norell .......................... 422/58 |
| 5,766,962 | A | | 6/1998 | Childs et al. ............... 436/518 |
| 6,140,136 | A | * | 10/2000 | Lee ............................. 436/518 |
| 6,228,657 | B1 | | 5/2001 | Genovese et al. .......... 436/167 |
| 6,382,409 | B1 | * | 5/2002 | Scala ......................... 206/5.1 |
| 6,524,857 | B1 | * | 2/2003 | Perkins ........................... 436/3 |

* cited by examiner

Primary Examiner—R. Alexander Smith
(74) Attorney, Agent, or Firm—Stephen R. Greiner

(57) ABSTRACT

An airborne hazard detector including a housing having a slot in a side thereof for receiving a sheet of M8 chemical detection paper and a principal opening in the top thereof for the passage of airborne chemical warfare agents to the sheet and for observing color changes in the sheet. The housing also has a number of secondary openings adjacent the principal opening. A number of manually rotatable dials is positioned within the housing with each being visible through one of the secondary openings. The dials bear indicia indicative of the time and date that the sheet of M8 chemical detection paper was last inspected.

8 Claims, 3 Drawing Sheets

AIRBORNE HAZARD DETECTOR

FIELD OF THE INVENTION

The present invention relates generally to analyzers, structured indicators, or manipulative laboratory devices and, more particularly, to test packages or kits.

BACKGROUND OF THE INVENTION

M8 chemical detection paper has become a staple in war zones throughout the world. This paper, as is well known, is treated with compounds that change color in the presence of airborne toxins. Thus, upon seeing a color change in the paper, a user can take appropriate precautions to minimize exposure to the toxins that may have been released by an enemy in a chemical attack.

M8 paper is distributed in pads containing twenty-five sheets. Since sheets torn from the pad have no anchoring means, they are susceptible to loss when deployed in the field. So, users have taken to taping individual sheets of M8 paper to vehicles, stanchions and other supporting surfaces. Unfortunately, M8 paper deployed in this manner is exposed to the weather where it deteriorates rapidly and is sometimes mistaken for refuse and is discarded by passersby. Furthermore, because M8 paper should not be contaminated by writing that might indicate its date of deployment, determining the time of a chemical attack can be difficult.

SUMMARY OF THE INVENTION

In light of the problems associated with the deployment of M8 chemical detection paper in the field, it is a principal object of the invention to provide an airborne hazard detector that will protect and support a sheet of M8 chemical detection paper at a fixed height above the ground. Thus, the hazard detector in accordance with the present invention prolongs the useful life of the M8 paper contained within itself by minimizing weathering and preventing inadvertent destruction by passersby.

It is another object of the invention to provide an airborne hazard detector of the type described that displays to a user, who may be a member of a military force or law enforcement agency, the last time that the detector was inspected. The display can be simply and manually updated as inspections occur to permit a user to gauge the time of a chemical attack.

It is a further object of the invention to provide an airborne hazard detector of the type described that is easy to set up in the field. The hazard detector requires neither special tools nor prolonged training to deploy. In fact, the hazard detector of this invention is believed to be particularly intuitive to use.

It is an additional object of the invention to provide an airborne hazard detector that is substantially impervious to chemical attack and is reusable. In the event of a chemical attack, the sheet of M8 paper within the hazard detector need only be removed and replaced for reuse of the detector. The hazard detector permits the easy replacement of sheets of M8 paper.

Yet another object of the present invention is to provide an airborne hazard detector that can support a sheet of M8 paper in a substantially horizontal orientation so that airborne chemical agents can rain down onto the sheet for enhanced detection capabilities.

It is an object of the invention to provide improved elements and arrangements thereof in an airborne hazard detector for the purposes described that is: compact in size, lightweight in construction, inexpensive to manufacture, substantially impervious to airborne chemical warfare agents and dependable in use.

Briefly, the airborne hazard detector in accordance with this invention achieves the intended objects by featuring a housing having a slot in one side thereof for receiving a sheet of M8 chemical detection paper and a principal opening in the top thereof both for the passage of airborne chemical warfare agents to the sheet and for observing color changes in the sheet. The housing also has a number of secondary openings adjacent the principal opening as well as a pair of apertures in its bottom and side. A number of manually rotatable dials is positioned within the secondary openings. The dials bear indicia indicative of the time and date that the sheet of M8 chemical detection paper was last inspected. The indicia is visible through the secondary openings. The detector also has a post with a blunt end that is capable of selective insertion into the aperture in the bottom of the housing for supporting the housing above the ground and a pointed end capable of selective insertion into the aperture in the side of the housing for storing the post when it is not needed.

The foregoing and other objects, features and advantages of the present invention will become readily apparent upon further review of the following detailed description of the preferred embodiment as illustrated in the accompanying drawings.

BRIEF DESCRIPTION OF THE DRAWINGS

The present invention may be more readily described with reference to the accompanying drawings, in which.

Similar reference characters denote corresponding features consistently throughout the accompanying drawings.

DETAILED DESCRIPTION OF THE PREFERRED EMBODIMENT

Figure 1:
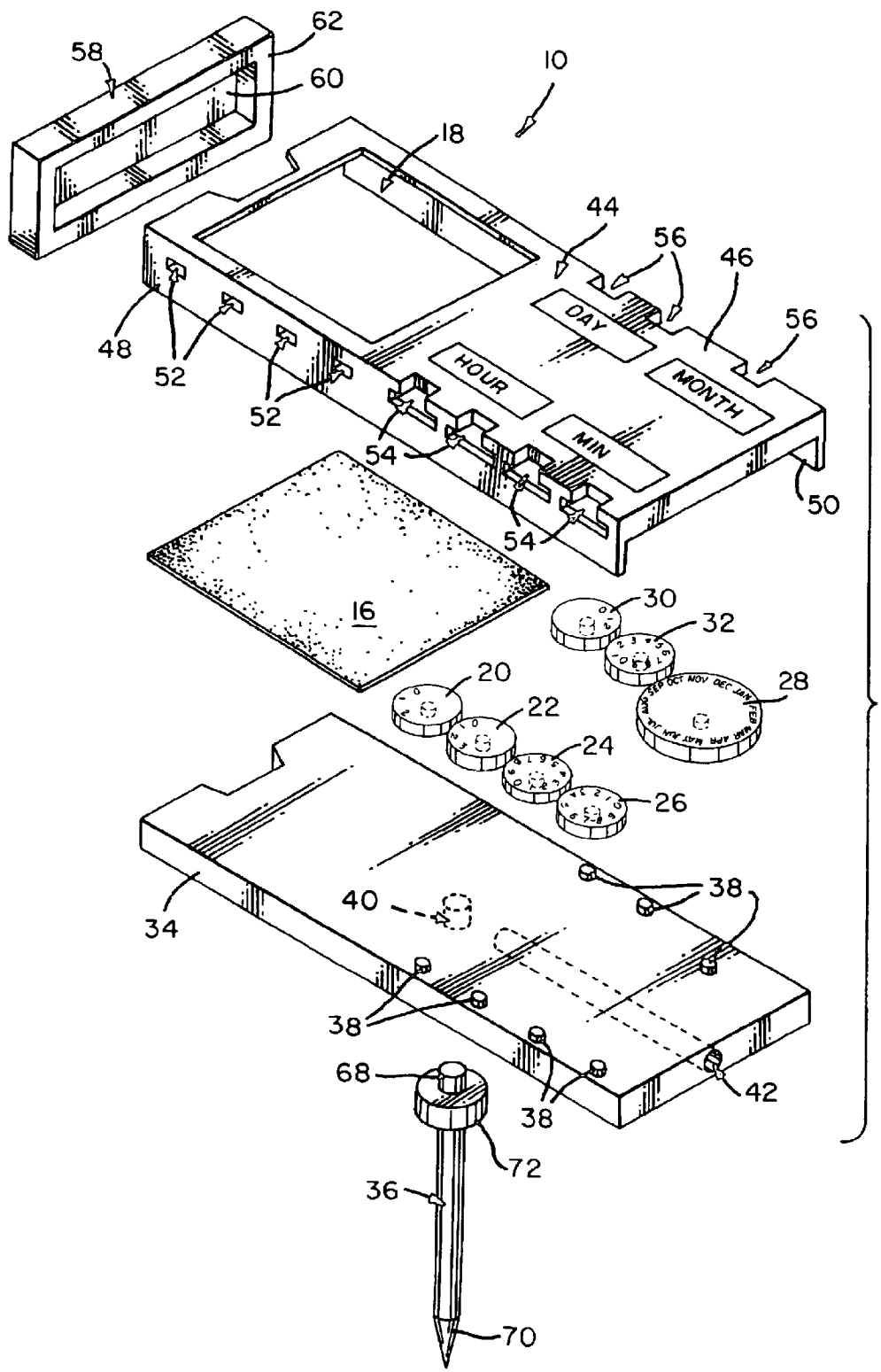
FIG. 1 is an exploded perspective view of an airborne hazard detector in accordance with the present invention.
Figure 2:
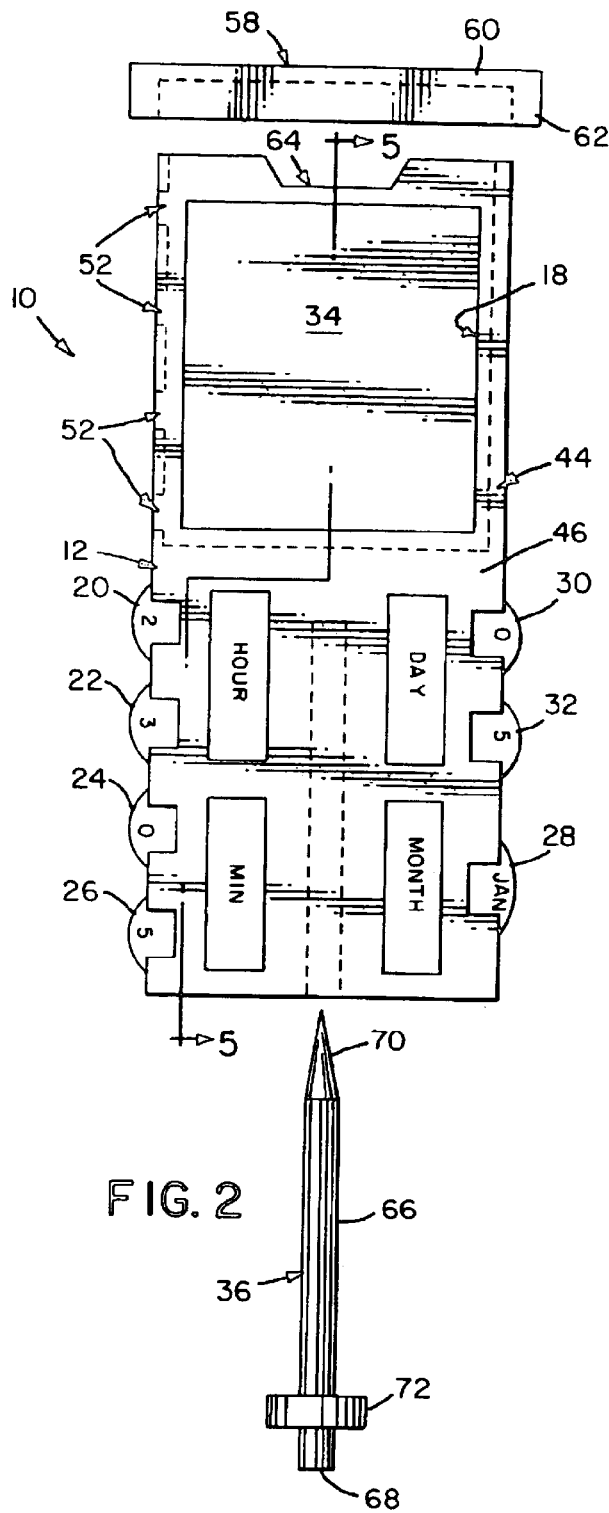
FIG. 2 is a top view of the airborne hazard detector of FIG. 1 with its end cap and support stake withdrawn from the detector body.
Figure 3:
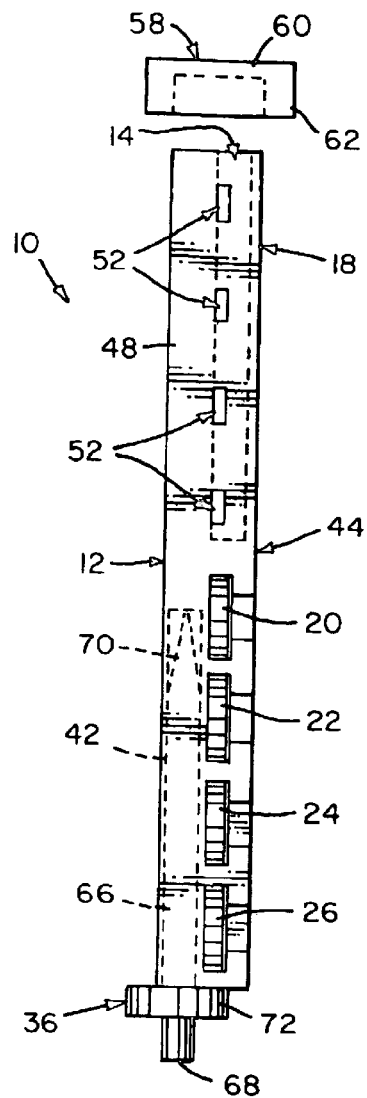
FIG. 3 is a side view of the airborne hazard detector with its end cap withdrawn from the detector body and its support stake inserted into the detector body.
Figure 4:
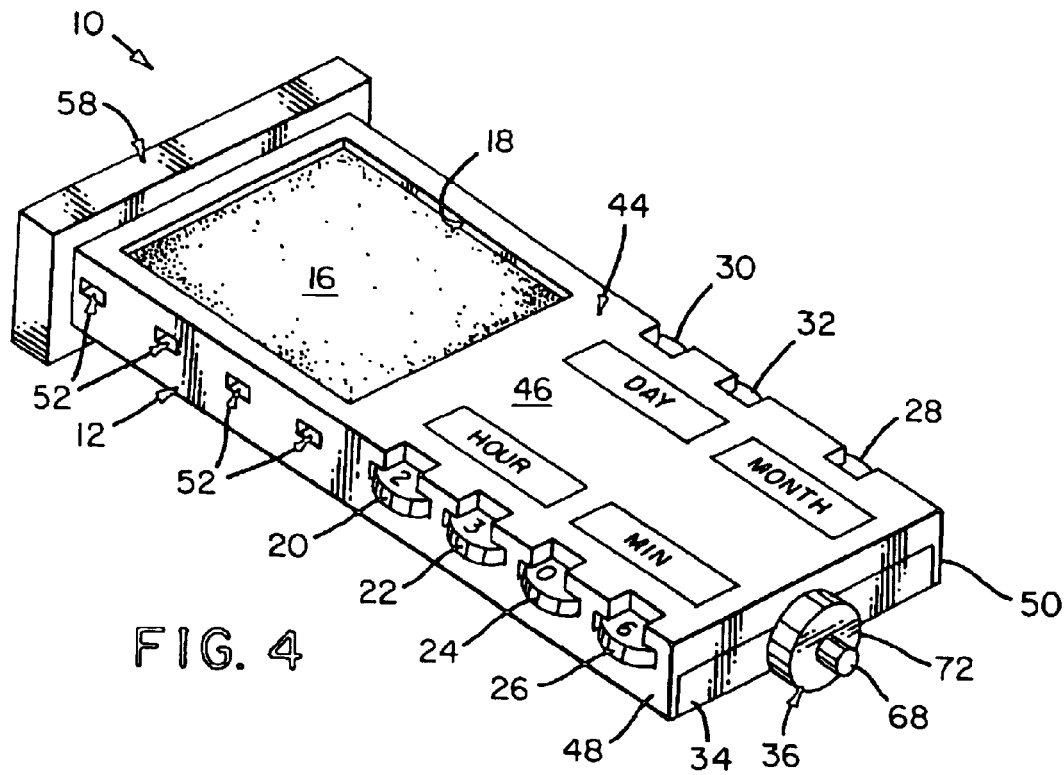
FIG. 4 is a perspective view of the airborne hazard detector with its end cap and support stake being carried by the detector body.
Figure 5:
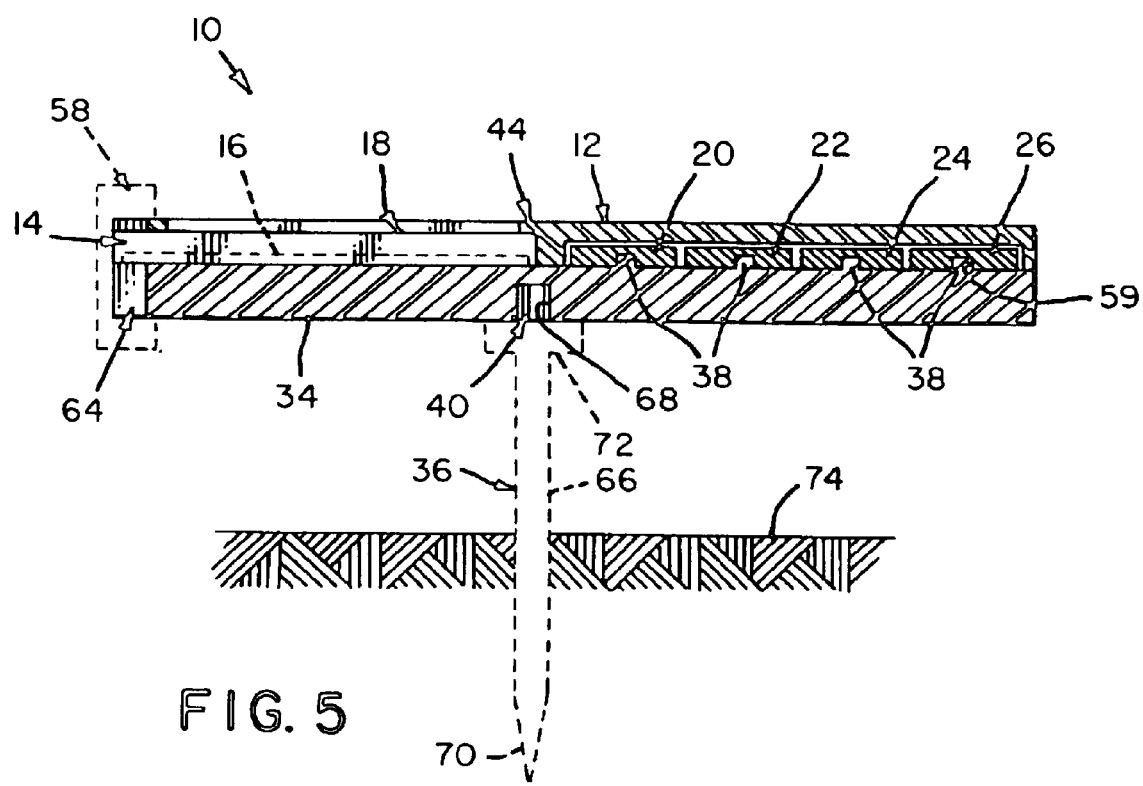
FIG. 5 is a cross-sectional view taken a long line 5—5 of FIG. 2 with the support stake holding the detector body above the ground.

Referring now to the FIGS., an airborne hazard detector in accordance with the present invention is shown at 10. Detector 10 includes a housing 12 having a slot 14 at one of its ends for receiving a sheet 16 of M8 chemical detection paper. A principal opening 18 in the top of housing 12 permits chemical warfare agents in the air to gain access to sheet 16 and permits any color changes in sheet 16 to be observed. A number of manually rotatable dials 20–32 positioned within housing 12 permit the time and date that sheet 16 was last inspected to be displayed.

Housing 12 is formed of plastic and includes a rectangular base plate 34 that carries dials 20–32 and receives a post 36. As shown, the top of base plate 34 has a number of pins 38 that extend upwardly to serve as axles upon which dials numeral 20–32 can rotate. An aperture 40 is provided in the bottom of base plate 34 into which the top of post 36 can be fitted for securing housing 12 to the ground during use. When not required, substantially all of post 36 can be fitted within another aperture 42 that extends inwardly from one side of base plate 34 to the center of base plate 34.

Housing 12 also includes a cover plate 44 having an inverted U-shaped configuration. Cover plate 44 includes a rectangular top portion 46 from the front and back of which a pair of side portions 48 and 50 extend downwardly to snap-fit against the front and back of base plate 34. Portions 46, 48 and 50 are dimensioned such that slot 14 is formed in housing 12 when cover plate 44 is fitted atop base plate 34.

Cover plate 44 is provided with a number of openings 18, 52, 54 and 56. For example, opening 18 is provided in top portion 46 to provide access to slot 14. Openings 52, however, are provided in side portion 48 to serve as drains for any precipitation that might fall through opening 18 and onto sheet 16 during use of hazard detector 10. Additionally, openings 54 are provided in both the top and side portions of 46 and 48 for access to dials 20–26. Openings 56 are provided in both the top and side portions 46 and 50 for access to dials 28–32.

Dials 20–32 are plastic disks with recesses as at 59 in their centers for receiving pins 38. Dials 20–26 are positioned on pins 38 along the front of base plate 34 so as to project through openings 54. Dials 20 and 22 are used together to indicate the hour of the day, in military time, that the hazard detector 10 was last inspected. So, dial 20 bears the numerals 0, 1 and 2 on its top and dial 22 bears the numerals 0, 1, 2, 3, 4, 5, 6, 7, 8 and 9 on its top. Dials 24 and 26, however, are used together to indicate the minutes of the hour in which hazard detector 10 was last inspected. Dial 24, therefore, bears the numerals 0, 1, 2, 3, 4 and 5 on its top and dial 26 bears the numerals 0, 1, 2, 3, 4, 5, 6, 7, 8 and 9 on its top. Each of the numerals on dials 22–26 can be rotated for independent viewing in openings 54.

Dials 28–32 are positioned on pins 38 along the back of base plate 34 so as to project through openings 56. Dial. 28 is used to indicate the month in which hazard detector 10 was last inspected. Dial 28 bears indicia: "Jan," "Feb," "Mar," "Apr," "May," "Jun," "Jul." "Aug." "Sep," "Oct," "Nov" and "Dec" about its top indicative of the twelve months of the year. Dials 30 and 32, on the other hand, are used together to indicate the particular day of a month that hazard detector 10 was last inspected. Thus, dial 30 bears the numerals 0, 1, 2 and 3 on its top and dial 32 bears the numerals 0, 1, 2, 3, 4, 5, 6, 7, 8 and 9 on its top. Each of the dials 28–32 can be independently rotated so that indicia related to a month and day can be observed through openings 56.

An optional cap 58 is formed of plastic and is releasably fitted over one end of housing 12 to close slot 14 and prevent the loss of sheet 16 when detector 10 is deployed in windy environments. Cap 58 has a rectangular end wall 60 from which a peripheral side wall 62 extends. Side wall 62 is dimensioned to snugly engage both cover and base plates 34 and 44 and hide notch 64 formed therein for the easy withdrawal of sheet 16 from slot 14.

Post 36 is formed of plastic and can be used to support housing 12 above the ground. Post 36 includes an elongated rod 66 that has opposed blunt and pointed ends 68 and 70. A peripheral flange 72 extends outwardly from rod 66 at a location closely adjacent blunt end 68. Blunt end 68 can be selectively and snugly fitted within aperture 40 in the bottom of base plate 34 for holding detector 10 above the ground 74. When not needed, pointed end 70 can be selectively inserted within aperture 42 in the side of base plate 34 for storage.

Use of airborne hazard detector 10 is straightforward. First, the stored post 36 is withdrawn from aperture 42 in housing 12 and its end 68 is inserted in aperture 40 for deployment. Next, pointed end 70 of post 36 is pushed into the ground 74 by applying a gentle downward pressure to the top of housing 12. Then, a sheet 16 of M8 paper is inserted fully into slot 14 in housing 12 and cap 58 is pressed into position on housing 12 to close slot 14. Finally, dials 20–32 are manually rotated to indicate the time and day that detector 10 was deployed in the field for use.

Hazard detector 10 must be deployed prior to an attack to ensure that sheet 16 is in a position to determine the presence of a chemical warfare agent. Preferably, a detector 10 would be placed at each corner of a building meant to be guarded thereby. During a release of chemical warfare agents, particles thereof rain slowly downward, through opening 18 and onto sheet 16. Compounds carried on sheet 16 change color when contacted by the chemical warfare agents permitting users to determine whether they are under attack and when the attack may have been initiated.

After a suspected attack, sheet 16 is examined to learn whether an actual release of a chemical warfare agent has occurred. If sheet 16 has changed color, the time and date indicated by dials 20–32 should be noted, and sheet 16 should be removed and replaced in accordance with the steps outlined above for deploying detector 10. If sheet 16 has not changed color, sheet need not be replaced unless it is believed to have been exposed to excessive weathering. In either case, however, dials 20–32 should be rotated to identify the new date and time that sheet 16 was inspected. Detector 10 is now ready for reuse.

While the invention has been described with a high degree of particularity, it will be appreciated by those skilled in the art that modifications may be made thereto. For example, double-sided tape (not shown) can be employed with housing 12 to secure detector 10 to a smooth surface such as an automobile bumper for the protection of travelers. Therefore, it is to be understood that the present invention is not limited to the sole embodiment described above, but encompasses any and all embodiments within the scope of the following claims.

We claim:

1. An airborne hazard detector, comprising:
   a housing having a slot in a side thereof for receiving a sheet of M8 chemical detection paper and a principal opening in the top thereof for the passage of airborne chemical warfare agents to the sheet and for observing color changes in the sheet, said housing also having a plurality of secondary openings adjacent said principal opening; and,
   a plurality of manually rotatable dials each being positioned within one of said secondary openings, said dials bearing indicia indicative of the time and date that the sheet of M8 chemical detection paper was last inspected, said indicia being visible through said secondary openings.

2. The airborne hazard detector according to claim 1 further comprising a sheet of M8 chemical detection paper positioned within said slot.

3. An airborne hazard detector, comprising:
   a housing having a slot in a side thereof for receiving a sheet of M8 chemical detection paper and a principal opening in the top thereof for the passage of airborne chemical warfare agents to the sheet and for observing color changes in the sheet, said housing also having a plurality of secondary openings adjacent said principal opening and an aperture in its bottom;

a plurality of manually rotatable dials each being positioned within one of said secondary openings, said dials bearing indicia indicative of the time and date that the sheet of M8 chemical detection paper was last inspected, said indicia being visible through said secondary openings; and, a post being selectively inserted within said aperture for supporting said housing above the ground.

4. The airborne hazard detector according to claim 3 further comprising a sheet of M8 chemical detection paper positioned within said slot.

5. The airborne hazard detector according to claim 3 further comprising a cap releasably fitted over said housing to close said slot.

6. An airborne hazard detector, comprising:

a housing having a slot in a side thereof for receiving a sheet of M8 chemical detection paper and a principal opening in the top thereof for the passage of airborne chemical warfare agents to the sheet and for observing color changes in the sheet, said housing also having a plurality of secondary openings adjacent said principal opening as well as a first aperture in its bottom and a second aperture opposite said slot;

a plurality of manually rotatable dials each being positioned within one of said secondary openings, said dials bearing indicia indicative of the time and date that the sheet of M8 chemical detection paper was last inspected, said indicia being visible through said secondary openings; and, a post having a blunt end and a pointed end, said blunt end being capable of selective insertion into said first aperture for supporting said housing above the ground and said pointed end being capable of selective insertion into said second aperture for storing said post.

7. The airborne hazard detector according to claim 6 further comprising a sheet of M8 chemical detection paper positioned within said slot.

8. The airborne hazard detector according to claim 7 further comprising a cap releasably fitted over said housing to close said slot and prevent the loss of the sheet of M8 chemical detection paper positioned within said slot.

* * * * *